United States Patent [19]

Moore et al.

[11] Patent Number: 4,669,465

[45] Date of Patent: Jun. 2, 1987

[54] LASER CATHETER CONTROL AND CONNECTING APPARATUS

[75] Inventors: Gary L. Moore, Minneapolis; Bruce H. Neilson, Brooklyn Park; James V. Kauphusman, Champlin; James S. Sharrow, St. Louis Park, all of Minn.

[73] Assignee: GV Medical, Inc., Minneapolis, Minn.

[21] Appl. No.: 679,633

[22] Filed: Dec. 10, 1984

[51] Int. Cl.⁴ ............................................. A61B 17/36
[52] U.S. Cl. ................. 128/303.1; 128/395; 128/398; 219/121 L; 219/121 LA
[58] Field of Search ............ 128/303.1, 395–398, 128/303.15, 344, 6–8, 656, 658; 219/121 L, 121 LA

[56] References Cited

U.S. PATENT DOCUMENTS

| | | | |
|---|---|---|---|
| 2,857,915 | 10/1958 | Sheridan | 128/658 |
| 3,399,668 | 9/1968 | Lundgren | 128/658 |
| 3,801,766 | 4/1974 | Morrison, Jr. | 128/303.14 |
| 3,877,838 | 4/1975 | Choy | 128/344 |
| 4,006,736 | 2/1977 | Kranys et al. | 128/655 |
| 4,026,284 | 5/1977 | Boehringer | 128/205.24 |
| 4,060,724 | 11/1977 | Heine et al. | 128/398 |
| 4,146,019 | 3/1979 | Bass et al. | 128/395 |
| 4,175,545 | 11/1979 | Termanini | 128/6 |
| 4,279,252 | 7/1981 | Martin | 128/658 |
| 4,418,688 | 12/1983 | Loeb | 128/6 |
| 4,422,457 | 12/1983 | Hattori | 128/6 |
| 4,438,765 | 3/1984 | Wilinsky | 128/395 |
| 4,445,892 | 5/1984 | Hussein et al. | 128/303.1 |
| 4,448,188 | 5/1984 | Loeb | 128/395 |
| 4,470,414 | 9/1984 | Imagawa et al. | 128/303.1 |

FOREIGN PATENT DOCUMENTS

| | | | |
|---|---|---|---|
| 0074914 | 3/1983 | European Pat. Off. | 128/303.1 |
| 2647618 | 10/1976 | Fed. Rep. of Germany | 128/303.1 |
| 2945080 | 5/1981 | Fed. Rep. of Germany | 128/303.1 |

*Primary Examiner*—Kyle L. Howell
*Assistant Examiner*—Ruth S. Smith
*Attorney, Agent, or Firm*—Orrin M. Haugen; Thomas J. Nikolai; Frederick W. Niebuhr

[57] ABSTRACT

A multi-lumen laser enhanced transluminal angioplasy catheter apparatus provided with a balloon or expandable member which is coupled to a catheter connecting manifold member providing a plurality of inlet ports for handling and delivering procedure-dependent materials. A laser fiber advance unit, in turn, controllably advances and couples the lasing fiber between the catheter manifold and a laser control unit. The fiber advance unit provides interlock means preventing actuation or operation of the control unit, unless and until the tip of the laser beam transmitting fiber extends beyond the distal end of the catheter, and means are provided for controlling the insertion extent of advancement of the laser fiber and its transmitting tip into the body of the catheter.

19 Claims, 8 Drawing Figures

U.S. Patent  Jun. 2, 1987  Sheet 1 of 3  4,669,465

LASER CATHETER CONTROL AND CONNECTING APPARATUS

BACKGROUND OF THE INVENTION

The present invention relates to angioplasty catheters and in particular to laser enhanced transluminal angioplasty catheters which include apparatus for controlling the insertion of the catheter, insertion of the laser fiber into the catheter, and the introduction of procedure-dependent or procedure-enhancing fluids to the site of a blood vessel occlusion within a patient being treated.

The laser catheter control and connecting apparatus of the present invention is particularly adapted for use in combination with laser enhanced transluminal angioplasty catheter devices, with these devices having been found useful in treatment of some forms of arteriosclerosis. The laser enhanced catheter devices are useful for treatment of certain types of obstructions or occlusions formed or created in blood vessels which as plaque build-up or the like, with exposure to laser beam energy being undertaken in order to obtain either a partial removal, reduction and/or the elimination of the obstruction by means of such exposure. An optical fiber member is utilized for transmitting or conducting a beam of laser energy from a generator onto an output lens for delivery of the laser energy onto or against the plaque or other matter obstructing or occluding a blood vessel. The extent of exposure to laser beam energy may be controlled by selecting and regulating the extent of on-time of the laser and the power level, with the monitoring of the procedure being accomplished by means of the catheter control system and fluoroscopy. Based upon their proven effectiveness, laser enhanced transluminal angioplasty catheter devices are considered valuable tools for the treatment of commonly encountered forms of arteriosclerosis and the like.

Atheroclerosis is among the more commonly encountered forms of arteriosclerosis as it relates to the human heart and circulatory system and has typically been treated with drugs, angioplasty catheterization, and more traumatic open heart bypass surgical procedures or even in amputation of limbs with diseased peripheral vessels. Of these various forms of treatment, angioplasty catheterization has been found to be a treatment of choice in certain situations. Such treatment normally involves bringing a balloon-tipped catheter proximal to the obstructing material in the vessel, with the dilation balloon portion of the catheter normally being positioned across the obstruction. The balloon portion is thereafter inflated so as to cause dilation of the obstruction.

In many cases, this procedure is effective in reopening the blood vessel and restoring substantially normal circulation. This procedure is, however, especially dependent upon the skill of the physician, and particularly as that skill pertains to manipulation and ultimate direction and control of the catheter. Normally, some assistance or guidance is provided the physician through fluoroscopy techniques, typically through the incorporation of radiopaque members at each end of the balloon member. Angioplasty catheterization is, however, frequently limited to those patients having obstructions which have not already totally occluded the blood vessels to a point where the distal tip of the catheter would otherwise be prevented from either entering or passing through the obstruction prior to dilation of the obstruction.

By way of further background, some examples of some known dilating catheters can be seen in U.S. Pat. Nos. 4,040,413; 4,271,839; and 4,299,226. Some examples of catheter devices including optical fibers can also be seen in U.S. Pat. Nos. 3,123,066; 3,136,310; 3,858,577; 4,146,019; and 4,273,109. Still further, examples of laser enhanced catheters can be seen in U.S. Pat. Nos. 3,467,098; 3,538,919; 3,843,865; and 4,266,548.

Because of the foregoing limitations and various other perceived deficiencies in each of the catheters described in the above-mentioned patents, the assignee of the present invention has undertaken the development of a laser enhanced transluminal angioplasty catheter. This device is disclosed in co-pending commonly assigned application, Ser. No. 560,234, filed Dec. 12, 1983, entitled "LASER TRANSLUMINAL ANGIOPLASTY CATHETER".

SUMMARY OF THE INVENTION

An improved catheter and insertion apparatus is provided for use in a laser-enhanced transluminal angioplasty system. The system comprises a multi-lumen angioplasty catheter, at least two manifolds for the catheter including a balloon catheter manifold and a laser enhancement fiber manifold, a lasing fiber advance unit, an electronic control unit, the laser generator, and means within the catheter for the delivery of procedure-dependent or procedure-enhancing fluids. In use, the application of laser beam energy through the catheter is controlled via the control unit in association with a hand-held fiber advance unit and whereby controlled amounts and durations of exposure to laser beam energy may be applied at a controlled zone or location within the patient.

In the system of the present invention, the inflatable balloon catheter and its manifold is a stand-alone system and is arranged to function in standard percutaneous transluminal angioplasty as well as percutaneous transluminal coronary angioplasty (PTA/PTCA) procedures. The laser enhancement fiber manifold is adapted to be interconnected with and function in combination with the balloon catheter manifold, to create an overall system with added capability. When the manifolds are so interconnected, the overall system functions as a laser enhanced transluminal angioplasty balloon catheter. Operational safety is increased by virtue of the arrangement of the components facilitating the interconnecting operations, with certain of these interconnecting operations being undertaken to achieve appropriate sub-system alignment prior to the time that laser beam energy may be delivered through the system. For example, to enhance product safety, the utilization of a balloon catheter with a specific length may only be used with a matching and mating energy transmitting laser enhancement fiber. Unless matching components are selected, the pertinent housing elements may not be interconnected nor locked together, and the laser portion of the system remains disabled.

In connection with the present invention, the balloon catheter manifold comprises an assembly for connecting the lumens of the multi-lumen balloon angioplasty catheter to the lasing fiber and also to a means for the delivery of procedure-dependent or procedure-enhancing fluids or drugs. A plurality of branch luer fittings provide communication or accessibility for administering procedure-dependent fluids or drugs to the patient through lumens formed within the catheter. An associated proximal connector and septum seal further assist in the coupling and sealing of a guide wire or the lasting fiber to the catheter.

The portion of the system for advancing the lasing fiber through the catheter comprises a hand-held gripping member which controls the insertion or extent of advance of the lasing fiber relative to the distal tip of the catheter. The hand-held member further is provided with a control switch which is actuated when lasing is to be initiated. The catheter advance portion or unit includes:

(a) means interlocking the catheter manifold with the laser advance unit housing so as to prevent inadvertent actuation of the laser until the lasing fiber advance unit has been properly interconnected to the balloon catheter;

(b) means for establishing a zero reference point when the tip of the lasing fiber is properly positioned relative to the tip of the balloon catheter and when operation of the laser may be undertaken without risk of damage to the body of the catheter;

(c) means for controlling the depth of insertion of the lasing fiber relative to the distal tip of the balloon catheter; and (d) means for initiating operation of the laser so as to commence lasing.

In various alternative embodiments of the present invention, a pressure relief valve may be provided for controlling the inflation pressure of the catheter balloon. In other embodiments, vessel occluding and catheter centering balloons may be provided along the body of the catheter. Still further, a plurality of radiopaque markers may be and preferably are provided at predetermined locations along the laser beam transmitting fiber for facilitating monitoring of the location of the transmitting fiber tip relative to the location of the catheter tip.

The present invention in combination, makes available a number of new features to a laser-enhanced transluminal angioplasty catheter, the features facilitating the actual insertion of the catheter, the insertion and advance of the lasing fiber within the catheter, and the delivery of procedure-dependent or procedure-enhancing fluids into and through the catheter. In another aspect of the present invention, improved control is provided over the positioning of the lasing fiber while it is in use. Further, the present invention makes available an integrated set of controls so that the attending cardiologist or physician is able to direct his attention to the proper and direct control of the initiation, duration, and extent of application of the lasing energy to the selected site within the patient's body.

The system of the present invention provides a unique combination of features for a laser-enhanced transluminal angioplasty catheter, including an interlock for improved control of the laser system, the utilization of a coupling and sealing arrangement which is available in the catheter manifold system, and the availability of a number of ports in the catheter manifold system for introduction of fluids during the lasing procedure. The catheter and its associated systems and components provides a means for incorporating radiopaque markers into the catheter structure, thereby enhancing the ability of the cardiologist or physician to properly position the catheter and the fiber carrying the lasing energy as well as to properly monitor and control the operation of the lasing system. For example, the lasing fiber may be extended or advanced beyond the tip of the catheter device for a predetermined distance, with this advancement being undertaken at the direction and under the control of the physician. The presence of radiopaque markers on the catheter and on the fiber, provides appropriate information to the cadiologist or physician with respect to the specific location of the various components including the catheter and those components contained therewithin. Also, the system includes an appropriate control feature which prevents firing of the laser unless the lasing fiber is in a proper position relative to the distal tip of the catheter so as to avoid the problem of having the laser energy damage the catheter structure. This control feature is generally referred to as the "zeroing" feature for lasing fiber positioning control and functions as a built-in interlock system preventing inadvertent laser actuation when the lasing fiber is in its retracted position. In addition to the "zeroing" control feature, actuation means are provided in the hand-held member for causing retraction of the lasing fiber into the catheter when the lasing procedure has been completed.

Therefore, it is a primary object of the present invention to provide an improved laser-enhanced transluminal angioplasty catheter device which is adapted for undertaking standard percutaneous transluminal angioplasty procedures as well as percutaneous transluminal coronary angioplasty procedures with the further ability of undertaking such procedures with efficacious laser enhancement.

It is a further object of the present invention to provide an improved laser enhanced transluminal angioplasty catheter apparatus which comprises a system having safety features which control and monitor the operation of the lasing portion so as to avoid the problem of having the laser energy damage the catheter structure.

It is yet a further object of the present invention to provide an improved system for a laser-enhanced transluminal angioplasty catheter apparatus which is provided with means for controlling the positioning of the laser transmitting fiber within the catheter assembly, and wherein the catheter device as well as the lasing fiber is provided with radiopaque markers to permit proper monitoring and control of the operation of the system.

It is yet a further object of the present invention to provide an improved laser-enhanced transluminal angioplasty catheter system which is adapted for use with lasing fibers and catheter assemblies of varying lengths, and wherein coupling arrangements are provided which permit introduction of only lasing fibers of appropriate length within a given catheter member.

The above objects, advantages and distinctions of the present invention, as well as its construction, will become more apparent upon reference to the following description of the preferred embodiment thereof with respect to the appended drawings. Before referring thereto, it is to be recognized that the invention is described only with respect to its presently preferred embodiment and its various presently contemplated modifications. Accordingly since other modifications may be made to these embodiments without departing from the spirit and scope of the invention, the following description should not be interpreted to in any way be a limitation upon the scope of the present invention.

IN THE DRAWINGS

DESCRIPTION OF THE PREFERRED EMBODIMENT

Figure 1:
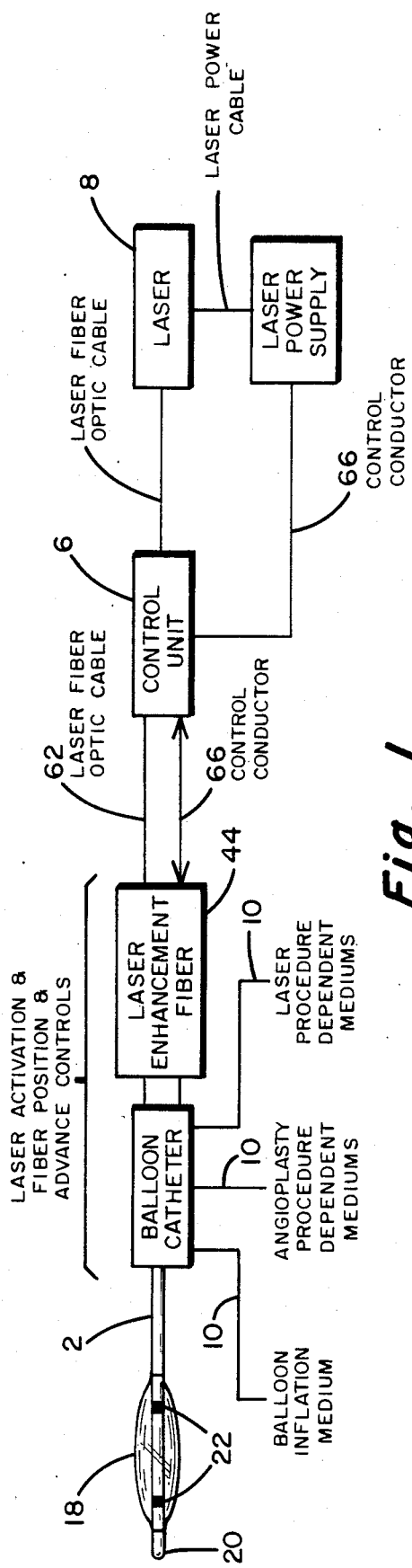
FIG. 1 is a block diagram of the laser-enhanced transluminal angioplasty catheter system of the present invention.

Referring to FIG. 1, this is a block diagram of a laser-enhanced transluminal angioplasty catheter system embodying features of the present invention. In particular, the system of the invention as illustrated in FIG. 1 comprises a percutaneous transluminal angioplasty catheter that may be, when need is indicated, provided with a laser enhancement capability. The laser enhancement requires the availability of a laser generator equipped with a suitable power supply, a control, as well as a means for delivering the energy through an appropriately selected optical fiber. The fiber is normally positioned within the inflatable balloon catheter, with the activation of the laser and the control thereof being achieved through the control unit, as indicated.

Figure 2:
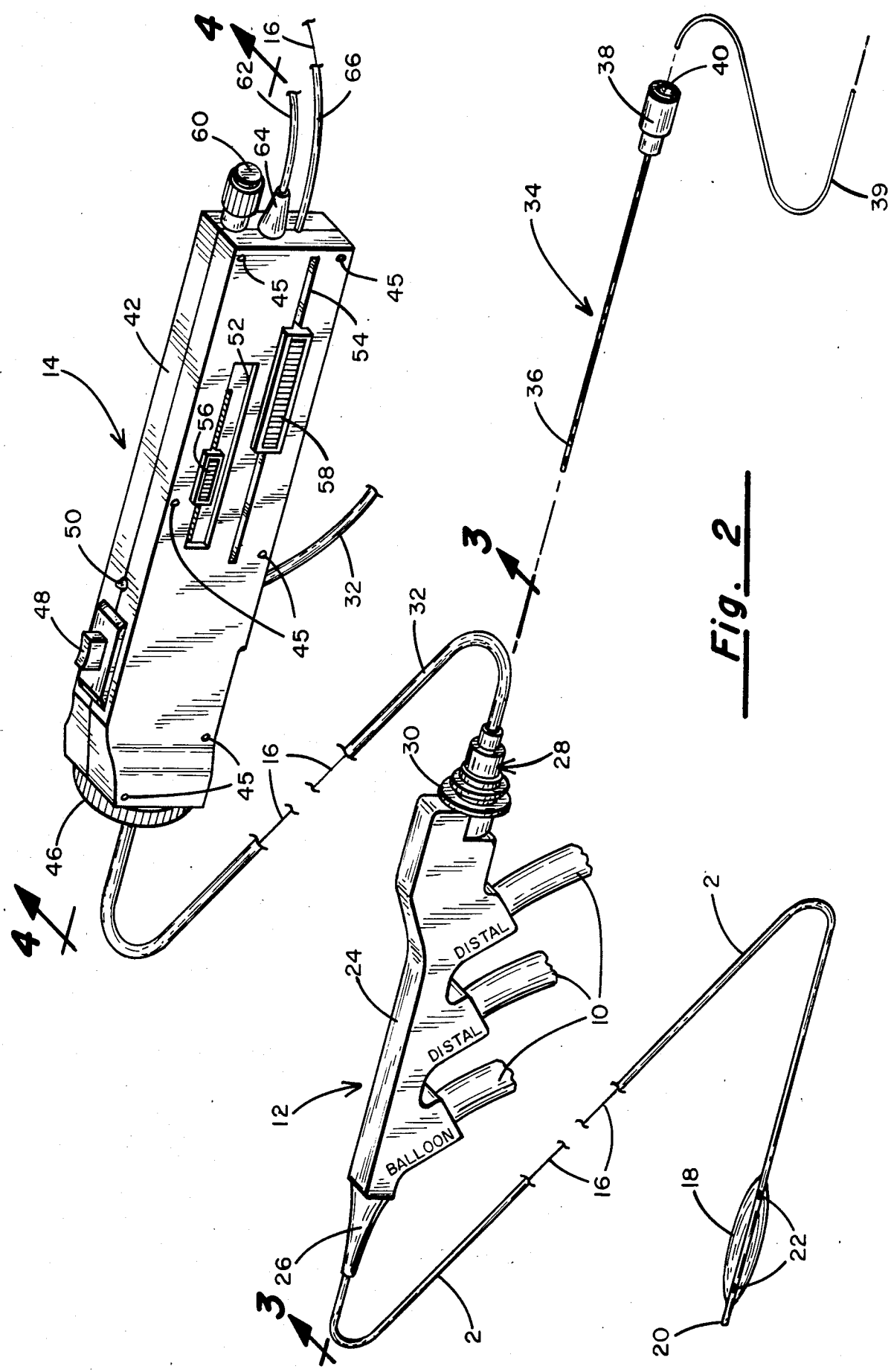
FIG. 2 is a perspective assembly view of the catheter manifold and catheter advance portions of the apparatus from the block diagram of FIG. 1.

The angioplasty balloon catheter 2 is operatively coupled to a fiber positioning and advance control means designated, for simplicity, a catheter manifold unit 12 and a fiber advance manifold unit 14 such as illustrated in FIG. 2 in spaced-apart position. As more fully explained hereinafter, the catheter manifold unit 12 and the fiber advance manifold unit 14 are arranged to be coupled together so as to form a unitary catheter manifold/fiber advance manifold hand-held unit. In the schematic illustration of FIG. 1, certain fiber positioning and advance control means are collectively shown schematically at 44 in the box labeled "Laser Enhancement Fiber" for purposes of simplicity. In addition, the system includes an electronic control unit 6 and its subordinant laser 8. An appropriate balloon inflation medium is operatively coupled to the balloon catheter 2 to achieve inflation, when desired. In addition, procedure-dependent materials such as radiopaque dyes, flushing agents and drugs are arranged to be administered through the catheter 2 upon introduction through conduits 10-10, each of which communicates with a lumen formed in the catheter and which are arranged for delivery of such materials through orifices disposed at the distal tip end of the catheter. An associated laser beam conducting or "optical" fiber extends from the laser 8 to the distal tip end of the catheter. The proximal segment or end of the fiber is coupled by means of a continuing electro-optic connection from laser 8 to the control unit 6 and thence to an optical fiber with portions or segments of its length normally being retained within the catheter 2 and with other portions or segments passing through the catheter manifold unit 12 and fiber advance manifold unit 14. Appropriate interlocking control conductors, in turn, functionally couple the control unit 6 to the catheter manifold unit 12 and fiber advance manifold unit 14 in order to provide for appropriate overall control.

As should be apparent, the present invention in lieu of a conventional system arrangement with an independent control for each of the various inputs, instead provides for a hybrid, centralized control so as to facilitate and enable the attending physician to undertake and control a number of individual operations or functions as required throughout any procedure primarily from a separate hand-held gripping member which is described more fully hereinafter. Principally, the system centralizes the electronic and/or mechanical controls for the system, including those controls pertinent to the operation of the laser 8, those pertinent to the dispensing of one or more mediums to promote the laser function, and those associated with the imaging or locating functions. One or more of these systems are normally ongoing and operational during most procedures. In this way, the laser-enhanced transluminal angioplasty catheter system of the present invention combines the operation and control of several sub-systems into a single safe and effective operational system. In the physical arrangement of the system of the present invention, each functional operation is essentially continuously under the direct control of the physician, and he is not required to make extraneous movements or become familiar with the operation of each of the variety of the different equipment types present. While an overall system arrangement is provided, it will be appreciated that the balloon catheter portion may be used independently, with the balance of the sub-systems, including particularly the laser being utilized in combination with the balloon catheter to provide a complete operational apparatus or system. In certain embodiments of the present invention, it is normally desirable to provide an imaging capability, which would normally be present as a centralized imaging device arranged to be operatively coupled to the lasing fiber so as to assist in its positioning function and its control. For example, a viewing screen may be utilized in some systems, with the viewing screen being coupled to an electro-optical arrangement with imaging elements being received within the body of catheter 2 so as to permit imaging or viewing of the site from the distal tip of the catheter. Conventional fluoroscopic viewing is, of course, useful and normally employed in the operation of the system of the present invention.

For further information relative to the details of the control unit 6 as well as other features of the system, attention is directed to the invention described in the previously-mentioned co-pending U.S. patent application of the present assignee entitled "Laser Transluminal Angioplasty Catheter". Attention is also directed to that certain copending application entitled "LASER CATHETER FEEDBACK SYSTEM", Ser. No. 679,920, filed Dec. 10, 1984 on even date herewith, and wherein the control apparatus preferably employed in combination with the laser subsystem of the present apparatus along with its function is disclosed.

Referring to FIG. 2, there is shown a perspective assembly view of the system of the present invention including the balloon catheter 2 in mounting relation to the catheter manifold assembly 12 and to the fiber advance manifold assembly 14. The fiber handling features of these two manifold assemblies collectively comprise the fiber position advance controls shown schematically at 44 in FIG. 1. In use, the catheter manifold assembly 12 and the fiber advance manifold assembly 14 facilitate the insertion of the lasing fiber 16 into catheter 2 as well as the delivery of procedure-dependent inflation medium, drugs, fluids, and the like through the conduits 10-10 formed within catheter 2. Furthermore, the fiber advance manifold assembly 14 physically couples the proximal end of catheter 2 to the laser transmitting fiber 16, and functionally interlocks the catheter fiber combination to the control unit 6 to prevent premature or inadvertent operation or activation of the laser, while at the same time permitting controlled alignment or positioning of the laser transmitting fiber within the catheter and also relative to the catheter tip. In this fashion, full operator control is maintained over the positioning of the catheter so as to achieve the desired depth of insertion of the catheter fiber combination, while at the same time preventing inadvertent activation of the laser. Laser activation must not occur while the tip of the lasing fiber is retracted within the catheter.

In terms of its general construction, the catheter 2 essentially comprises a multi-lumen, balloon tipped antioplasty catheter. In the preferred embodiment, at least two lumens are provided, one supplying an inflating medium to the balloon member 18 and the other dispensing various procedure-dependent materials or fluids through the conduits 10-10 to a central lumen terminating in a port at the distal tip 20 of the angioplasty catheter 2. Aspiration may also be accomplished through this series of lumens and conduits. Associated radiopaque markers 22 secured or mounted on the catheter body or structure facilitate catheter insertion monitoring and control of enabling fluoroscopic or other similar viewing. One or more radiopaque tip markers (not shown) may be provided internally of the tip 20 to further facilitate locating the various functional elements or components of the system relative to one another and to the obstructed site in the vein. For example, the fiber is located relative to the distal tip of the catheter 2, with both the fiber and the tip being, in turn, located relative to the occlusion in the vein. Radiopaque markers are normally incorporated under the balloon porting in order to locate the balloon, with such markers typically being used with known balloon catheters. As it is presently contemplated, the angioplasty catheter 2 includes two lumens, one with a diameter of either 4 french or 5 french for catheter lengths of from 100 to 140 centimeters and with a diameter of 7 french for catheter lengths of 80 and 100 centimeters. These sizes and lengths are believed to be sufficient for the needs of most situations and applications, it being understood that the present invention is applicable to catheters of any size. It is recognized that additional lumens can be provided, as necessary, but since the addition of each lumen increases the catheter diameter, the application of the catheter of the present invention to certain procedures may become limited when the number of lumens is increased. In lieu thereof, it has been found that the lumens provided can serve multiple purposes by appropriately controlling their sequence of use through flushing with non-interactive fluids between successive injections of fluids. In this way several procedure-dependent fluids may be delivered through only one or two of conduits 10 and associated lumens.

With attention now being directed to the catheter manifold assembly 12, this device comprises a molded body member 24 with the distal end thereof being attached to a clear silicone strain relief member 26. An identification tube (not shown) may be secured or mounted about the angioplasty catheter 2 on which a catheter identification number is displayed. Mounted at the proximal end of the catheter manifold assembly 12 is a threaded connector assembly or block 30 having a means arranged to receive a forward portion 28 of protective tubular sleeve member 32. Tubular sleeve member comprising a coaxial fiber connector 32 is integral with forwardly extending portion 28, with portion 28 being coupled to connector assembly 30. In those circumstances when the balloon catheter assembly and laser enhancement fiber are not interconnected, portion 28 remains part of the laser enhancement fiber system. In the arrangement illustrated in FIG. 2, portion 28 and assembly 30 are mated with each other, and a sealing arrangement, as discussed hereinbelow, is designed to prevent retrograde fluid flow.

Connector assembly 30 is keyed or otherwise mechanically coded with connector 28 in accordance with the catheter length so as to controllably match the specific catheter selected for use with a laser energy transmitting fiber of the correct length. Therefore, a 100 centimeter catheter may only be connected to a mating 100 centimeter fiber. The threaded connector block 30 is an integral part of the catheter manifold assembly 12. A plurality of fluid supply conduits 10-10 are shown with one being adapted to be coupled to the balloon inflation fluid port and with the other ports of the catheter manifold assembly 12 designated "distal" being adapted to be coupled to the other fluid sources. In the present embodiment, the balloon inflation fluid port is arranged in communication with the catheter lumen extending to the balloon 18. The remaining conduits 10-10 each communicate with the central lumen and ultimately with a port at the distal tip 20 of the angioplasty catheter 2. An associated sealing septum (shown at 88 in FIG. 3 and mounted slightly forward of the connector block 30) prevents retrograde flow, and will be discussed in detail hereinafter.

In association with the catheter manifold assembly 12, a hollow tubular guide wire introducer 34 is also provided. Guide wire or introducer 34 comprises an elongated tubular member 36 having a rearwardly mounted coaxial plastic insertion member 38 with a conically formed aperture 40 formed internally thereof for facilitating the insertion of a guide wire shown at 39 during the insertion of the angioplasty catheter 2 into and along the selected blood vessel. The guide wire introducer 34 is used to initially penetrate the septum seal and when in place extends beyond the location of a number of interconnections within the catheter manifold assembly 12 to the various conduits 10. This arrangement provides a smooth uninterrupted tubular path, whereby the guide wire may be directed axially into the center of the catheter distal lumen as desired.

In the event it has been determined that exposure to laser beam energy is indicated, the angioplasty catheter 2 containing guide wire 39 is initially disposed in place within the selected blood vessel. The introducer 34 and the guide wire 39 are then withdrawn from the catheter and thereafter the forward portion 28 of coaxial fiber connector 32 is attached to the outer end of connector block 30. Forward portion 28 of coaxial fiber connector 32 is provided with an introducer tube (not shown) similar in function to elongated tubular member 36, and which likewise protrudes part way into the septum seal 88 to prevent retrograde flow around fiber 16. Upon completion of attachment of the forward portion 28 to the connector block 30, the laser fiber 16 is appropriately passed through the septum seal and introduced within and advanced along the catheter 2. Because of the relatively precise mating of forward portion 28 with connector block 30, particularly with respect to their internal construction, fiber 16 is introduced into and moved through the system. At this point, it is to be noted that the connector block 30 essentially comprises a connector member that includes means for receiving a tubular female portion 28 being secured by means of a pair of locking studs 90-90 on the connector block 30. Locking is achieved upon twisting or rotating the outer female portion of connector 28 relative to the connector 30. The laser fiber introduction procedure will be described hereinafter.

With continued attention being directed to FIG. 2, laser fiber 16 is shown as being encapsulated coaxially within fiber connector or protective tubular coaxial sleeve member 32, with fiber connector or protective tubular sleeve member 32 being shown partially broken away. In the arrangement illustrated in FIG. 2, fiber 16 is also shown as being partially inserted into angioplasty catheter 2. Surrounding the laser fiber 16 proximally of catheter manifold assembly 12 is a protective tubular sleeve member 32 that is secured at one end to the connector block 30 by the female connector 28 and received in sliding relation to the fiber advance unit manifold assembly 14. While the tubular sleeve member 32 is mounted in sliding relation to the fiber advancing unit 14, the laser fiber 16 is mounted in semi-fixed relation to the fiber advancing unit 14. Upon coupling the tubular sleeve 32 through the female connector 28 to connector block 30 and sliding the fiber advance unit manifold assembly 14 forward or to the left as shown in FIG. 2, the laser fiber 16 is caused to move or progress through the center lumen of the catheter 2 as sleeve 32 passes through the rear or proximal end of the fiber advance unit manifold assembly 14.

A discussion of the details of the fiber advance unit manifold assembly 14 is now appropriate. Specifically, this component of the system comprises a two part molded hand holdable gripping member 42, preferably fabricated of plastic. The two halves of member 42 are held together by a number of screws 45 passing therebetween. As an alternative to the utilization of screws 45, suitable adhesive cement, or an ultrasonic sealing process may be utilized to bond the two half segments together. Mounted along the forward end of the fiber advance unit manifold assembly 14 is a rotatable locking nut 46 that releasably mounts in threaded relation to the mating threaded portion of the connector block 30. The forward end of the fiber advance unit manifold assembly 14 is positioned in bearing relationship against the rearward end of the catheter manifold 12. The internal threads of locking nut 46 are arranged to be engaged upon the externally threaded portion of connector 65 block 30. Mounted along the top surface of the fiber advance unit manifold assembly 14 is a "laser initiate", pushbutton switch 48 and a lasing fiber "zero position" light emitting diode 50. For purposes of safety, pushbutton switch 48 is provided with a compound motion requirement for activation, with this motion requiring the pushbutton portion to be pressed both downwardly and to the right as shown in FIG. 2 in order to activate the laser. This dual motion is intended to prevent accidental or inadvertent activation of the laser. Also, it is spring-loaded in order to automatically return to its off position when finger or thumb pressure is released or removed. Light emitting diode 50 is energized to confirm that the distal tip of lasing fiber 16 is disposed axially outwardly of the distal tip 20 and angioplasty catheter 2 in accordance with details discussed hereinafter.

A finger-actuable fiber stop slide 56 along with fiber-advance slide 58 are slidably mounted relative to a pair of slots 52 and 54 formed through the opposed sides of the fiber advance unit manifold assembly 14. In the embodiment of FIG. 2, fiber advance slide 58 is designed to be finger-actuatable, it being understood that this finger-actuable slide member may be replaced with a power-driven system operated through and driven by other components of the control system in response to predetermined or pre-set drive controlled parameters. The appropriate parameter may be selected and programmed into the logic of the control unit, if desired. The movement of the fiber 16 may be appropriately accomplished by presently available hand controls. With respect to the pre-set drive parameters, the magnitude of the incremental fiber advance may be related to the rate of removal of plaque, tissue and/or other material involved.

Mounted along the rearward end surface of the fiber advance unit manifold assembly 14 is a "zero adjust" knob 60, a control conductor sheath 62 having a strain relief member 64 and another segment of the lasing fiber 16 which is retained within the tubular sheath 66. The segment of laser fiber 16 and the various control conductors contained within the sheathes 62 and 66, are operatively coupled to the control unit 6. In the preset embodiment and as previously mentioned, provisions may be made for imaging through additional optical fibers disposed in a lumen formed in catheter 2, while such imaging features are not specifically shown here. When the imaging feature is provided, segments of the appropriate conductors and other elements dedicated to achieve this function would typically be contained within sheath 66, and appropriately directed both distally and proximally of control unit 6. For example, the various optical fibers or conductors required to achieve the imaging function may be secured within molded body member 24 and extended to and operatively coupled to control unit 6 by requisite cable assemblies. Also, sensors such as ultrasonic sensors may be built into and disposed adjacent distal tip 20, if either required or desired to respond to certain conditions.

Figure 3:
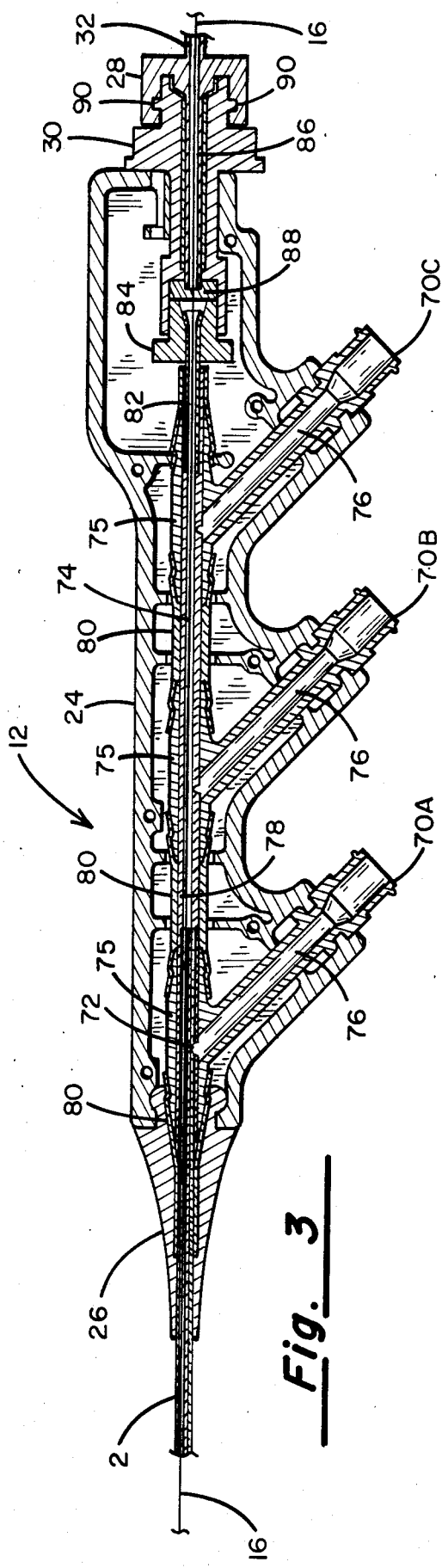
FIG. 3 is a cross-sectional view taken along section lines 3—3 of the catheter manifold portion of FIG. 2.
Figure 4:
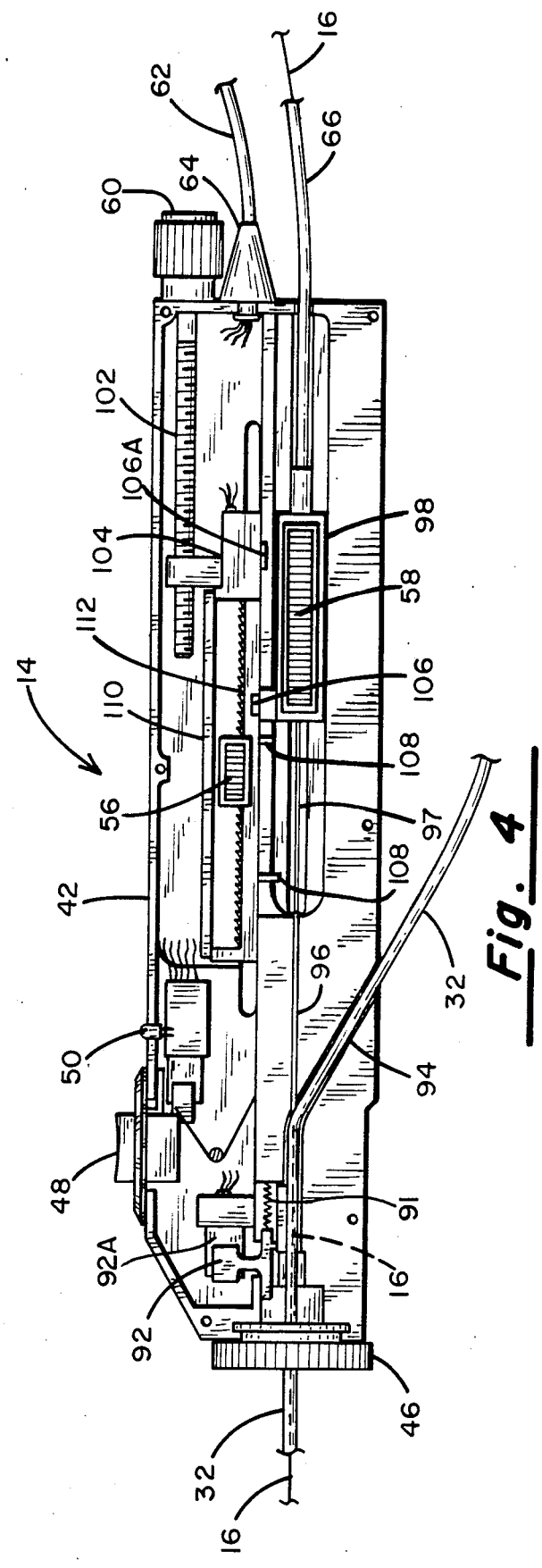
FIG. 4 is a side elevational view of the fiber advance unit of FIG. 2, with portions removed to reveal part of the inside thereof.

Turning attention now to FIGS. 3 and 4, the internal construction of the catheter manifold assembly 12, the fiber advance unit manifold assembly 14 and their operative inter-relationship will be described. FIG. 3 illustrates the details of construction of the catheter manifold assembly 12 and the manner in which the assembly 12 establishes communication with the lumens of the catheter 2. Specifically, a segment of angioplasty catheter 2 is axially coupled to the tip of the body member 24. A plurality of luers 70A, 70B and 70C are coupled to the extensions into which the individual lumens extend. Specifically, the leftmost or "balloon" luer 70A is coupled to the radially outwardly disposed lumen 72 of the angioplasty catheter 2 so as to accommodate the flow of fluid to the catheter balloon to control inflation and deflation of the balloon member 18. Similarly, the central lumen 74 is coupled to the center and right-most "distal" luers 70B and 70C so as to permit the movement of fluids therethrough including the introduction of appropriate procedure-dependent fluids whenever indicated.

The communication between the catheter lumens 72 and 74 with the individual luers 70A, 70B and 70C is achieved by initially piercing the catheter 2 so as to exposure a portion of the outer lumen 72. The catheter 2 is thence inserted through a tubular opening formed in the upper horizontal portion 75 of the left-most "T"-like luer 70A so as to bring the pierced portion into alignment with the central channel 76 of the vertical portion of the luer 70A. The right-most end in lumen 74 is thence brought into coaxial relation with a surrounding center tubular member 78 that circumscribes the catheter without obstructing the pierced opening to the channel 76 of the left-most luer 70A. The tubular member 78 thence is passed through each of the horizontal portions 75 of the center and right-most luers 70B and 70C so as to bring separately formed pierced regions thereof into communication with the appropriate channels 76 formed in luers 70B and 70C. Thus, the "balloon" port is opened to and communicates with the lumen 72 and the "distal" ports are opened to and communicate with the central lumen 74. As the lumens of the catheter 2 are aligned with the appropriate luers 70A, 70B or 70C, appropriate lengths of thermally shrinkable tubing 80 are mounted over the flared ends of the horizontal portions 75 of each of the luers. Upon completing assembly and confirming the proper registration of each port to the appropriate lumen, such as lumen 72 or 74, the lengths of shrinkable tubing are heated so as to form a liquid and pressure-fast seal.

Prior to understanding to shrink tubing 80, however, the tubular member 78, which also comprises a length of thermally shrinkable tubing, is coaxially aligned with a first tubular metallic member 82. Tubular member 82 is centrally disposed within a seal locking cap 84 which mounts in locking coaxial relation with the left-most end of the connector block 30. A second metallic tubular member 86 is coaxially mounted in and forms a part of the body of connector block 30 such that upon inserting the locking cap 84 in the end of connector block 30, the tube members 82 and 86 are brought into coaxial registry. A silicone septum seal 88 mounted therebetween prevents retrograde flow. Further, the members 82 and 86 each have one of their ends flared to receive introducer 34 through the septum seal 88. Member 36 has a length sufficient to extend beyond the intersection of each of the luers 70A, 70B, and 70C with the internal bore. A pair of stud-like projections 90 extend from the right-most end of the connector block 30 for engaging mating notches formed in the forwardly extending portion 28 of coaxial sleeve 32.

Attention is directed to FIG. 4 which is a cross-sectional view of fiber advance manifold assembly 14. Mounted internally to the left-most end of assembly 14 and adjacent to the locking ring 46, is a sliding magnet portion 92 that activates a first Hall-effect interlock switch. Magnet 92 is slidably mounted so as to engage the right-most end or outer end of the connector portion 28 (FIG. 2) while the lasing fiber is being inserted into the catheter 2. Once the catheter manifold 12 abuts the fiber advance unit manifold assembly 14, the locking ring 46 may be rotated so as to threadably engage the threaded portion of the connector block 30. As the connector block 30 is drawn inwardly of locking ring 46, the magnet portion 92 is engaged by connector portion 28 and moved against the force of a biasing spring 91, to activate the first Hall-effect switch and a control signal is generated and sent to the control unit 6. Thus, unless and until magnet 92 is engaged by connector portion 28 drawn inwardly of locking ring 46, the interlock switch controlled by magnet 92 remains open, and the control unit 6 will not permit the operation of the laser 8. While various types of switches or detector devices may be utilized, the Hall-effect switch is preferred, since it provides a moisture-proof sealed system. In the event of a fluid leak within the system, this type of switching element will not be readily shorted out or otherwise disabled.

Mounted rearwardly of the magnet portion 92 and in communication with channel 94 formed in the body 42 of fiber advance unit manifold assembly, is a tubular guide member 96. A length of metallic tubing 97 is mounted coaxially in sliding relation to the guide member 96, with tubing 97 surrounding the laser transmitting fiber 16. Tubing 97 along with the laser fiber 16 is permanently attached to the left side of a sliding member 98. Attached to the other side of sliding member 98 is the protective sheath 66 mounted coaxially about the laser fiber 16. Thus, upon engaging the finger-actuated slide member 58 (reference to FIG. 2) overlying the sliding member 98, the slide member 98 may be moved laterally. Lateral movement of slide member 98 causes the laser transmitting fiber 16 to be advanced or retracted relative to the catheter 2 by means of the interacting guide members 96 and 97.

In use, the slide member 98 is caused to assume its right-most extreme position during the insertion of the laser fiber 16, with such position being maintained until the catheter manifold 12 and fiber advance unit manifold assembly 14 were actually secured to one another. At that point, too, and by design the tip of the laser fiber 16 would extend only to the distal tip 20 of the catheter 2 and would not extend outwardly therefrom. However, upon moving the slide member 98 to the left, the laser fiber 16 would be advanced beyond the distal tip 20. While normally under fluoroscopic viewing and monitoring, and when it has been determined that the outer distal tip of the laser fiber 16 is aligned with the previously mentioned radiopaque marker disposed internally of the distal tip 20 of angioplasty catheter 2, the attending physician would be aware that the laser fiber 16 may then be advanced further until the tip extends outwardly from the catheter 2 and into the blood vessel. This condition indicates to the operator that activation of the laser may proceed without concern for damage to the distal tip 20 of the catheter. However, actual lasing may not commence until the "zeroing" operation described below is completed.

As a precaution against catheter tip damage, the present invention includes a screw follower or substitutable slide member actuated interlock mechanism whereby the control unit 6 will not permit lasing until a "zero" location or condition for laser fiber 16 is established, with the "zero" condition corresponding to or representing the situation wherein the tip of the laser fiber is properly located relative to top 20, being represented by the energizing of light 50. Thus, upon obtaining a proper registration between the laser fiber 16 and catheter tip 20 by means of slide member 98, the zero adjust screw 102 is turned by rotating the zero-adjust knob 60 and thereby sliding carrier 104 is moved in either a forward or rearward direction. A magnetic actuating element 106 of a second Hall-effect switch 106A is disposed adjacent carrier 104. Magnetic actuating element 106 is mounted in the sliding member 98, with the other portion 106A being mounted in slide 104. When the magnetic actuating element 106 and Hall-effect switch 106A are brought into registration with one another, the second Hall-effect switch is closed, which in turn causes the light emitting diode 50 to become energized and thereby confirm the setting of the slide member 104 and the proper positioning the fiber 16 relative to the tip 20 of catheter 2.

The foregoing interlocks thus prevent the attending physician from activating the laser 8, until the system has confirmed that the catheter manifold assembly 12 and fiber advance unit manifold assembly 14 are in proper relative dispositions, one with the other, and that the tip of the laser fiber 16 is properly positioned relative to the tip 20 of the catheter 2. At this point too, it is to be noted that should the operator inadvertently move the slide member 98 from the zero position to the right so as to draw the tip of the lasing fiber inwardly of the catheter 2, the Hall-effect switch 106A associated with its magnet portion will cease energizing the light emitting diode 50 and activation of the control unit 6 under these circumstances will be prevented. By moving the slide member 98 to the left past the zero position, however, the operator is able to begin lasing at any desired time. The specific point at which it is desired that lasing may be commenced typically depends upon a confirmation by the physician that the placement of the lasing tip relative to the occlusion is proper, as viewed fluoroscopically. At that point, the attending physician typically sets a desired power level and lasing duration at the control unit 6, before activating the laser 8 via the pushbutton switch 48. As lasing proceeds and the operation progresses, the operator typically will move the slide member 98 to the left and thereby cause the tip of the lasing fiber to advance through the occluding substance. At this time too, a lasing medium is being introduced coaxially to the lasing fiber via the lumen 74 so as to provide an acceptable lasing medium and also to carry away the lased debris, thereby keeping the laser fiber tip and the immediately adjacent zone substantially free of such debris.

The physical arrangement of the various components of the present invention render it possible to locate virtually the entire operational portion of the apparatus within the sterile field. The laser may be fired and energy carried directly through the catheter. With the various interlocks present, the firing can be accomplished only when the system is entirely ready. Furthermore, the physical arrangement of the controls and the components renders the system essentially entirely physician dependent.

Various duty cycles for the laser are made available and the specific cycle desired may be selected therefrom. Typically, duty cycles or pulses of 1, 2, 5, 10, and 20 seconds duration may be provided. A period of quiescence is normally interposed between individual duty cycles, such as a period of at least about 2 seconds. During this quiescent period accidental re-activation of the system is prevented.

As indicated earlier, during operation of the laser, the dispensing of an appropriate medium such as saline solution into the site is desired. Such bolus dispensing is undertaking continuously during laser operation. Typically, the bolus rate is increased immediately prior to and during operation of the laser, with the increased rate being initiated a few seconds prior to firing or activation of the laser. This provides greater clarity of fluids during operation of the laser, particularly at the face or tip of the laser fiber, and also provides a better medium for the laser energy at the site. Because of the inherent elasticity of the catheter and the internal fluid pressure present, the increased bolus rate extends beyond the actual termination of the actual operation of the laser. Such continuation or extension of the increased rate is deemed to be desirable.

In order to control the depth of insertion of fiber 16 during operation of the laser, the present invention further provides a pair of stop members 108 and which act relative to the slide member 98 to limit the length of its movement to the left as viewed in FIG. 4. Specifically, a left-most fixed stop 108 is permanently mounted to the positioning means or member 104 to limit the maximum overall depth of insertion. An intermediate movably adjustable or slidable stop 56 is provided. To set stop member 56, it is necessary for the operator to lift the slidable stop 56 upwardly slightly against and toward the slide rail 110, against a spring (not shown) providing counter-force, so as to release the slidable stop 56 from its toothed engagement with the lower rail 112. The slidable stop 56 can them be moved a desired distance from the zero position. The operator is thus assured that upon moving the slide assembly 98 to the left, the stop 56 will prevent further movement. By successively advancing slide member 56, the occlusion can be incrementally removed. Alternatively, the operator may choose to adjust the slidable stop 56 to its left-most extreme position. Here, the maximum distance the laser fiber 16 can extend beyond the catheter is dependent upon tab stop 108. However, for most applications and in order to permit cooling to occur between individual operational cycles of the laser, the stop is sequentially moved. Also and as mentioned previously, where a sliding stop 56 is not required, the tab 108 associated with the positioning member 104 can be separated so as to permit unimpeded movement, except for the left-most stop 108. Typically, the laser fiber 16 is advanced a distance of 3 centimeters upon reaching the initial stop element 108, and with an advancement of 5 centimeters being possible upon advancing to the second or leftward-most stop 108.

Turning attention now to FIGS. 5 to 8, certain modifications to the foregoing apparatus are shown and which either separately or in combination further facilitate the use of the present invention. Specifically and referring initially to FIG. 5, this figure is taken through a pressure relief valve 120 such as may be used in conjunction with the "balloon" part of the catheter manifold assembly 12 to prevent exceeding the burst strength of the balloon member 18.

Because the balloon member 18 has an upper limit to its burst strength, care must be taken to avoid over-inflating of the balloon with the inflating medium such that the pressure limits thereof would be exceeded, causing it to burst or become excessively large. To prevent this problem from arising, a pressure relief valve 102 may be coupled to the flow channel 76 at the "balloon" port luer 70A such that upon detecting pressures just below the burst strength of the balloon or a pressure approaching the elastic limit of the material forming the balloon, the pressure exerted by a spring member 122 is overcome such that a ball seal or check valve poppet 124 is displaced to the left, creating an escape path via a port 126 in the valve 120. In this way, and independent of the regulation of the inflating medium during the inflation step, the attending physician is assured that the balloon will not burst or become excessively large, or assume an anomalous configuration.

Figure 6:
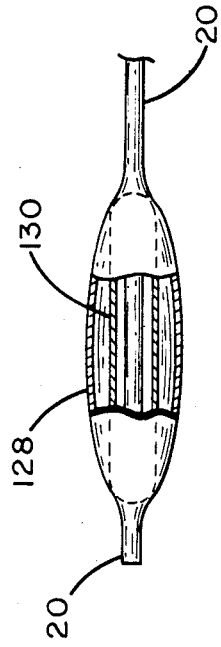
FIG. 6 is a detail fragmentary view of the distal section or portion only of the catheter, and illustrating the alternative embodiment of a coaxially arranged dual balloon catheter tip.
Figure 7:
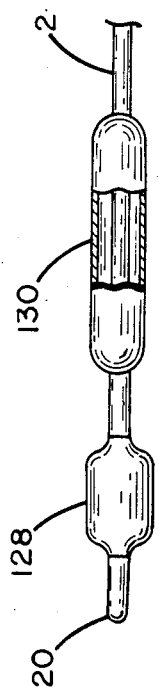
FIG. 7 is a detail fragmentary view of the distal section or portion only of the catheter, and illustrating the alternative embodiment of a serially or tandemly arranged dual balloon catheter tip.

With attention now being directed to FIGS. 6 and 7, alternative embodiments are disclosed for modifying the angioplasty catheter 2 to provide in lieu of a single balloon member 18, a pair of balloon members 128 and 130 for respectively permitting the occlusion of the blood vessel via the balloon member 128 to thereby block blood flow and accomplish the desired centering of the catheter within the occluded vessel by means of the balloon 130. With this concept in mind, FIG. 6 shows an arrangement which provides for a coaxial mounting of the balloon members 128 and 130 relative to the catheter 2. FIG. 7, by contrast, depicts the separate and adjacent mounting of the balloon members 128 and 130 along the catheter 2. While not shown in either FIGS. 6 or 7, it is to be recognized that various radiopaque markers may be provided as necessary so as to permit the physician to confirm the position or location of either or both of the balloons 128 and 130, along with the position of the marker containing tip.

Figure 8:
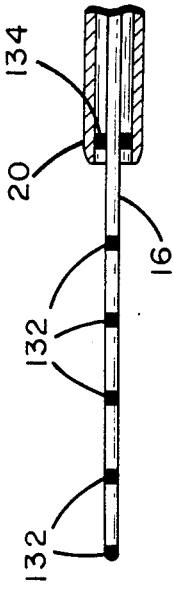
FIG. 8 is a fragmentary view, partially in section, and illustrating a lasing fiber tip having a plurality of axially spaced radiopaque index markers.
Figure 5:
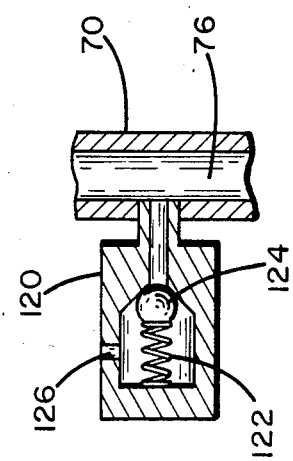
FIG. 5 is a cross-sectional view taken through a pressure relief valve adapted for use with the catheter manifold of FIG. 2.

In order to achieve the desirable feature of permitting the physician to determine the location of the tip of the laser fiber 16 relative to the tip 20 of the catheter 2, one such arrangement is illustrated in FIG. 8. This figure depicts a laser fiber 16 having a plurality of radiopaque markers 132 spaced axially therealong at predetermined distances from one another. The operator, upon establishing the zero position by means of the fiber advance unit manifold assembly 14 is thus able through fluoroscopic monitoring to view and determine the progression of the tip of the laser fiber 16 by observing the movement of its radiopaque marker 134 relative to the catheter tip 20. Thus, a visual confirmation of the rate of movement and/or distance progressed is obtained, over and above that similar or corresponding information obtained mechanically from slide assembly 59. Also, the attending physician is informed as to where the tip of the laser fiber 16 is positioned at all times.

From the foregoing, it should therefore be apparent that the present invention offers new and improved apparatus for controlling the insertion of a laser fiber into an angioplasty catheter within a selected blood vessel for treatment of an occlusion therein. It does so in a fashion which prevents damage to the catheter by premature or inadvertent laser activation. The present invention also provides a means for dispensing fluids to the site of the occlusion, and also restricts or avoids retrograde flow of fluids by means of septum seal 88.

While the present invention has been described with respect to its presently preferred embodiment and various modifications thereto, it is to be recognized that still other modifications may be made thereto without departing from the spirit and scope thereof. Accordingly, it is contemplated that the following claims shall be interpreted so as to including all those equivalent embodiments within the spirit and scope of the claimed invention.

What is claimed is:

1. Apparatus for treating obstructions in blood vessels, comprising in combination:

(a) a catheter having a proximal end and a distal end and a plurality of lumens extending from said proximal end toward said distal end, at least one of said lumens extending into said distal end and at least another one of said lumens opening to a first balloon member coupled to said catheter in proximity to said distal end;

(b) catheter manifold means coupled to said catheter and having a plurality of manifold ports, each of said manifold ports coupled to at least one of said catheter lumens for selective introduction and removal of procedure-dependent fluids;

(c) a laser generator, a laser energy conducting fiber operatively coupled to said laser generator, and fiber advance means, substantially fixedly coupled with respect to said fibers for advancing said laser energy conducting fiber through said manifold means to a point at least coincident with the distal end of said catheter, said fiber advance means including control means operatively coupled to said laser energy conducting fiber for preventing the operation of said laser generator until the distal tip of said laser fiber is positioned at a point at less coincident with the distal end of said catheter.

2. Apparatus as set forth in claim 1 including a sheath coupled slidably to said fiber advance means and in surrounding relation to a distal portion of said fiber extended distally of said fiber advance means; wherein said manifold means includes a connector means removably coupled to the distal end of said sheath; whereby the sliding of said fiber advance means, distally along and relative to said sheath advances the distal portion of said laser energy conducting fiber toward the distal end of said catheter axially through said sheath, through said manifold means, and then one of said lumens.

3. Apparatus as set forth in claim 2 wherein said connector means includes means for threadably coupling said fiber advance means to the catheter manifold means, upon sliding said fiber advance means, relative to said sheath, adjacent to the extreme distal end of said sheath.

4. Apparatus as set forth in claim 3 wherein said fiber advance means includes interlock means engageable with said connector means for preventing the delivery of laser energy to said fiber until said catheter manifold means and fiber advance means are threadably secured to one another.

5. Apparatus as set forth in claim 2 wherein said connector means includes seal means for isolating each lumen to prevent retrograde fluid flow through individual lumens during the administration of procedure-dependent pressurized fluids to certain predetermined another of said plurality of lumens of said catheter.

6. Apparatus as set forth in claim 2 wherein said fiber advance means includes a first slide means fixed to said fiber and slidable and adjustably positionable relative to said fiber advance means for advancing said laser energy conducting fiber within one of the lumens formed in said catheter and independently of said fiber advance means.

7. Apparatus as set forth in claim 6 including second slide means adjustably positionable relative to said fiber advance means for establishing a zero reference position relative to said first slide means when the distal tip of said laser fiber is in proximity to the distal end of said catheter.

8. Apparatus as set forth in claim 7 wherein said control means includes an actuating element coupled to said first slide means, and a switch responsive to said actuating element coupled to said second slide means, said second slide means being adjustably positioned whereby said first and second slide means are coincidentally positioned, thereby to actuate said switch, at said zero reference position.

9. Apparatus as set forth in claim 7 including a threaded screw means and follower means integral with said second slide means and threadably engaged with said screw means, and an operator adjustable knob coupled to said threaded screw means for advancing and retracting said second slide means relative to said fiber advance means.

10. Apparatus as set forth in claim 9 including adjustable stop means mounted in the path of travel of said first slide means for establishing a predetermined length of travel for said first slide means.

11. Apparatus as set forth in claim 9 including second stop means for establishing a maximum length of travel for said first slide means independent of said adjustable stop means.

12. Apparatus as set forth in claim 7 including means for visibly indicating when the distal tip of said laser fiber extends beyond the distal end of said catheter.

13. Apparatus as set forth in claim 12 wherein said fiber advancing means includes stop means positioned along a path of travel of said first slide means for limiting the travel of said laser energy conducting fiber to one or more predetermined stop points.

14. Apparatus as set forth in claim 1 wherein said fiber advance means includes means coupled to said laser source for initiating the operation of said laser source.

15. Apparatus for treating obstructions in blood vessels, comprising in combination:
(a) a catheter having a proximal end and a distal end and a plurality of lumens extending from said proximal end toward said distal end, at least one of said lumens being a laser energy conducting fiber receiving lumen and extending to said distal end, and at least another one of said lumens opening to a first balloon member coupled to said catheter adjacent said distal end;
(b) a laser source, a laser energy conducting fiber operatively coupled to said laser source, a manifold means coupled to said catheter and having a plurality of manifold ports, each of said manifold ports being coupled to at least one of said catheter lumens for selectively introducing and removing procedure-dependent fluids therethrough, said manifold means also including a connector means for coupling said manifold means to a sheath enclosing a portion of said laser energy conducting fiber therewithin;
(c) a fiber advance means substantially fixedly mounted relative to said fiber, and means for mounting said sheath slidably to said fiber advance means whereby the sliding of said laser energy conducting fiber advance means along said sheath toward a releasable coupling with said manifold means advances the distal end of said laser conducting fiber through said sheath, said manifold means, and toward the distal end of said catheter; a first slide means fixed to said fiber, mounted slidably relative to said fiber advance means, and thereby adapted for controlling the position of the distal tip of said laser energy conducting fiber relative to the distal end of said catheter independently of fiber advance means movement, said fiber advance means further including control means for preventing the operation of the laser source coupled to said laser energy conducting fiber until the distal tip of said laser conducting fiber is advanced to a predetermined location relative to the distal end of said catheter and said fiber advance means is so coupled with said manifold means.

16. A surgical kit for treating obstructions in blood vessels, comprising in combination:
(a) a catheter having a proximal end and a distal end and a plurality of lumens extending from said proximal end toward said distal end, at least a first of said lumens extending to said distal end and at least a second of said lumens extending to a first balloon member coupled to said catheter in proximity to said distal end;
(b) catheter manifold means coupled to said catheter and having a plurality of manifold ports, each of said manifold ports coupled to at least one of said catheter lumens for selective introduction and removal of procedure-dependent fluids;
(c) a guide wire; and guide means, adapted to be removably joined to said catheter manifold, for introducing said guide wire into said first lumen when so joined, to facilitate the insertion of said catheter into a selected vessel, said guide means including a guide tube insertable into and said manifold means for facilitating the introduction of said guide wire into said first lumen adjacent said manifold ports, and for facilitating removal of said guide wire from said first lumen after the introduction of said catheter into said selected vessel;
(d) a laser generator; a laser energy conducting fiber operatively coupled to said laser generator; and a fiber advance means, substantially fixedly mounted to said fiber, for advancing said laser energy conducting fiber through said manifold means and into said first lumen while said catheter is in said selected vessel and with said guide wire removed from said first lumen, said laser energy conducting fiber being advanced into said first lumen to a point at least coincident with the distal end of said catheter, said fiber advance means including means operatively coupled to said laser energy conducting fiber for preventing the operation of said laser generator until the distal tip of said laser fiber is positioned at a point at least coincident with the distal end of said catheter.

17. Apparatus as set forth in claim 16 including pressure relief means coupled to at least one port of said manifold for sensing fluid pressure within one of said catheter lumens, and including means for maintaining fluid pressure within said catheter lumen below a predetermined maximum.

18. Apparatus as set forth in claim 17 wherein said pressure relief means comprises a valve body including an input port, a check valve poppet resiliently biased to oppose fluid flow through said input port until a certain pressure is exceeded, and a relief port, said check valve poppet permitting the flow of fluid to said relief port, whenever the force created by the pressure of said procedure-dependent fluid exceeds the predetermined resilient force exerted against said check valve poppet.

19. Apparatus as set forth in claim 16 wherein at least one radiopaque marker is mounted adjacent the distal tip of said laser fiber at a first predetermined distance from the distal end thereof, and a further radiopaque marker on said catheter positioned a second predetermined distance from the catheter distal end, whereby an operator may fluoroscopically determine the relative separation between the distal tip of said fiber and the catheter distal end.

* * * * *

UNITED STATES PATENT AND TRADEMARK OFFICE
CERTIFICATE OF CORRECTION

PATENT NO. : 4,669,465

DATED : June 2, 1987

INVENTOR(S) : Gary L. Moore, et al

It is certified that error appears in the above-identified patent and that said Letters Patent is hereby corrected as shown below:

Column 16, line 16, "fibers" should read -- fiber --.
Line 23, "less" should read -- least --.

Column 18, line 12, "extending" should read -- opening --.
Line 24, "and" should be deleted.

Signed and Sealed this

Eighth Day of September, 1987

Attest:

DONALD J. QUIGG

Attesting Officer

Commissioner of Patents and Trademarks